（12） United States Patent
Arenas et al.

(10) Patent No.: US 12,066,398 B2
(45) Date of Patent: Aug. 20, 2024

(54) QUANTITATIVE MEASUREMENT OF MEMBRANE PROTEIN FUNCTION ON A BIOSENSOR

(71) Applicant: Nanotech Biomachines, Inc., Berkeley, CA (US)

(72) Inventors: Jaime E. Arenas, Berkeley, CA (US); William Emerson Martinez, Berkeley, CA (US); Monica Lozano, Berkeley, CA (US); Ngo Yim Wong, Berkeley, CA (US); Gertrude M. Gutierrez, Berkeley, CA (US)

(73) Assignee: William E. Martinez, Lake Forest Park, WA (US)

( * ) Notice: Subject to any disclaimer, the term of this patent is extended or adjusted under 35 U.S.C. 154(b) by 996 days.

(21) Appl. No.: 16/765,451

(22) PCT Filed: Jan. 12, 2018

(86) PCT No.: PCT/US2018/013537
§ 371 (c)(1),
(2) Date: May 19, 2020

(87) PCT Pub. No.: WO2018/132685
PCT Pub. Date: Jul. 19, 2018

(65) Prior Publication Data
US 2021/0382001 A1    Dec. 9, 2021

Related U.S. Application Data

(60) Provisional application No. 62/445,677, filed on Jan. 12, 2017.

(51) Int. Cl.
*G01N 27/414* (2006.01)
*G01N 27/327* (2006.01)
*G01N 33/543* (2006.01)

(52) U.S. Cl.
CPC ..... *G01N 27/4145* (2013.01); *G01N 27/3276* (2013.01); *G01N 27/4146* (2013.01); *G01N 33/5438* (2013.01)

(58) Field of Classification Search
CPC .......... G01N 27/4145; G01N 27/4146; G01N 27/327; G01N 27/3275–3278; G01N 33/5438
See application file for complete search history.

(56) References Cited

U.S. PATENT DOCUMENTS

| | | | | |
|---|---|---|---|---|
| 5,756,355 | A * | 5/1998 | Lang | G01N 33/5432 204/403.08 |
| 2010/0028681 | A1 * | 2/2010 | Dai | B82Y 40/00 252/301.16 |
| 2016/0324435 | A1 * | 11/2016 | Kuzum | A61N 1/0551 |

FOREIGN PATENT DOCUMENTS

EP    2848929 A1 *    3/2015    ........... G01N 33/543

OTHER PUBLICATIONS

Wang et al., "Charging the Quantum Capacitance of Graphene with a Single Biological IOn Channel," ACSNANO vol. 8, No. 5, pp. 4228-4238, Apr. 22, 2014 (Year: 2014).*

(Continued)

*Primary Examiner* — Alexander S Noguerola

(57) ABSTRACT

Disclosed herein are methods and devices for a cell-free assay platform that enables measurement of membrane protein function by measuring the events that are induced by ligand binding or other stimuli.

4 Claims, 7 Drawing Sheets

(56) References Cited

OTHER PUBLICATIONS

Zhou et al., "Detection of single ion channel activity with carbon nanotubes," Scientific Reports 5:9208 DOI:10.1038/srep09208, Mar. 17, 2015 (Year: 2015).*

* cited by examiner

QUANTITATIVE MEASUREMENT OF MEMBRANE PROTEIN FUNCTION ON A BIOSENSOR

CROSS-REFERENCE TO RELATED APPLICATIONS

This application claims priority to U.S. Provisional Patent Application No. 62/445,677, filed Jan. 12, 2017, the content of which is incorporated by reference in its entirety.

FIELD OF THE INVENTION

The invention relates to methods and devices for a cell-free assay platform that enables measurement of membrane protein function by measuring the events that are induced by ligand binding or other stimuli.

BACKGROUND OF THE INVENTION

A significant portion of targets for drug discovery are membrane proteins, including integral membrane proteins (IMPs) which have one or more hydrophobic domains embedded in the lipid bilayer of the cell membrane as well as hydrophilic domains that are exposed to the extracellular and intracellular spaces. These IMPs act as a means of communication between the extracellular and intracellular spaces carrying signals and transporting molecules between the two compartments.

The binding of ligands to IMPs can be effectively characterized by a number of cell-free biochemical assays using purified IMPs or membrane vesicle preparations and ligand. These include radioimmunoassays and biophysical methods such as surface plasmon resonance (SPR) and calorimetry. However, these methods cannot measure the functional response of the IMP upon ligand binding, which is typically done in cumbersome and expensive cell based assays that take considerable time. Furthermore, the data obtained from cell-based assays is convoluted and can be difficult to interpret as they only measure an end point that is the result of numerous events in the signal transduction cascade.

Currently, there are no suitable cell-free assays that can effectively evaluate the ability of ligands to affect the function of IMPs and to distinguish agonists from antagonists and inactive ligands. Thus, there is a need for such technology in the drug discovery industry and such technology will significantly improve the drug lead selection and characterization process.

SUMMARY OF THE INVENTION

Various aspects disclosed herein may fulfill one or more of the above-mentioned needs. The systems and methods described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for improved systems and methods.

Provided herein are the device and methods for a cell-free assay platform which enable measurement of membrane protein function by measuring the events that are induced by ligand binding, such as conformational changes, molecular interactions, enzymatic reactions and their products, changes in compartment ion concentrations caused by the movement of ions or metabolites through ion channels and transporters, and other responses. The device and methods provided herein also enable distinguishing agonists from antagonists and inactive ligands.

In a first aspect, provided herein is a device, comprising: a support substrate; a graphene layer, the graphene layer deposited on the support substrate; a functionalization layer, the functionalization layer deposited on at least a portion of the graphene layer; a lipid bilayer comprising: an upper leaflet surface, a lower leaflet surface and a hydrophobic interior volume bounded by the upper leaflet and the lower leaflet surfaces; a membrane protein associated with the lipid bilayer; a spacer molecule interposed between the lipid bilayer and the functionalization layer; and electrodes in electrical contact with the graphene layer, the electrodes adapted to detect an electrical signal from the graphene layer, wherein the spacer molecule establishes a distance between the lipid bilayer and graphene layer, wherein the distance permits detection of an electrical signal associated with a functional or structural change in the membrane protein upon binding of a test agent to the membrane protein.

In some embodiments, the functionalization layer comprises solid state material.

In some embodiments, the membrane protein is an integral membrane protein. In some other embodiments, the membrane protein is a peripheral membrane protein. In some other embodiments, the membrane protein is in native state.

In various embodiments, the distance established by the spacer molecule allows for differential analysis of an electrical signal arising from below the lower leaflet surface and an electrical signal arising from above the upper leaflet surface. In some of these embodiments, the differential analysis is sufficient to screen out the electrical signal detected from above the upper leaflet surface.

In certain embodiments, the spacer molecule comprises a chemical linker. In some of these embodiments, the chemical linker is covalently linked to the functionalization layer. In some other of these embodiments, the chemical linker is non-covalently linked to the functionalization layer.

In certain embodiments, the spacer molecule comprises a polymer. In some of these embodiments, the polymer comprises a polypeptide or a protein. In various embodiments, the molecular weight of the polypeptide or protein ranges from 1,000 Dalton to 500,000 Dalton. In some other of these embodiments, the polymer comprises a polyethylene glycol. In various embodiments, the molecular weight of the polyethylene glycol ranges from 500 Dalton to 40,000 Dalton. In certain other embodiments, the spacer molecule comprises a nanoparticle.

In some embodiments, the device comprises a binding interaction between the spacer molecule and the lower leaflet surface. In some other embodiments, the device comprises a binding interaction between the spacer molecule and the hydrophobic interior volume. In yet some other embodiments, the device comprises a binding interaction between the spacer molecule and the upper leaflet surface.

In various embodiments, one or more additional linkers are present between the spacer molecule and the lipid bilayer.

In certain embodiments, the distance between the upper leaflet surface and the graphene layer is greater than the sensing distance of the device. In certain embodiments, the distance between the lower leaflet surface and the graphene layer is less than or equal to the sensing distance of the device. In some of these embodiments, the distance between the lower leaflet surface and the graphene layer is less than the sensing distance of the device. In certain embodiments, the distance between the lower leaflet surface and the graphene layer is larger than the sensing distance of the device.

In various embodiments, the distance between the upper leaflet surface and the graphene layer is greater than the sensing distance of the device, and the distance between the lower leaflet surface and the graphene layer is less than or equal to the sensing distance of the device.

In certain embodiments, the sensing distance is empirically determined. In certain embodiments, the sensing distance is calculated.

In various embodiments, the sensing distance is between 0.5 nm to 100 nm. In certain embodiments, the sensing distance is between 0.5 nm to 50 nm. In certain embodiments, the sensing distance is between 0.5 nm to 25 nm. In certain embodiments, the sensing distance is between 0.5 nm to 15 nm. In certain embodiments, the sensing distance is between 0.5 nm to 10 nm.

In another aspect, provided herein is a method for assaying a functional interaction between a test agent and a protein bound to a lipid bilayer, comprising: exposing the test agent to the protein under conditions that promote binding of the test agent to the protein; and measuring an impact of the exposing on an electrical signal detected from the graphene layer.

In some embodiments, the measuring the impact comprises detecting a change in the electrical signal following the exposing. In some other embodiments, the test agent binds to the protein and measuring the impact comprises detecting no change in the electrical signal following the exposing.

In some embodiments, the method further comprises quantifying the impact based on the change in the electrical signal following the exposing. In some of these embodiments, the change indicates the test agent agonizes a function of the protein. In some other of these embodiments, the method further comprises exposing the protein to a ligand, and wherein the change indicates the test agent competes for binding to the protein with the ligand, and the test agent either affects or does not affect a function of the protein. In certain embodiments, the protein is exposed to the ligand prior to exposing the test agent to the protein. In certain embodiments, the protein is exposed to the ligand concurrent to exposing the test agent to the protein. In certain embodiments, the protein is exposed to the ligand post to exposing the test agent to the protein. In some embodiments, the change indicates the test agent antagonizes a function of the protein. In various embodiments, the method further comprises characterizing the test agent as an agonist, an antagonist, or an inactive ligand for the protein based on the measured impact of the exposing on the electrical signal.

In various embodiments, the function is a transport function or a signal transduction function. In certain embodiments, the transport function is an ion transport function, a nutrient transport function, a metabolite transport function, or a drug transport function. In certain embodiments, the signal transduction function comprises an enzymatic reaction step. In some of these embodiments, the enzymatic reaction step comprises a protein phosphorylation step, a protein dephosphorylation step, an ATP hydrolysis step, a GTP hydrolysis step, a cAMP formation step, a phospholipase reaction step, or a protease reaction step. In certain embodiments, the signal transduction comprises a conformational change. In certain embodiments, the signal transduction comprises the formation or disruption of a molecular interaction. In some of these embodiments, the molecular interaction is a protein-protein interaction. In some other of these embodiments, the molecular interaction is between a protein and a lipid, a sugar, a metabolite, a nucleotide, or an ion.

In another aspect, provided herein is a method for tuning the device, comprising: adjusting the size of the spacer molecule or the number of stacked spacer molecules, to affect the distance between the graphene layer and the surface of the lower leaflet of the lipid bilayer; and measuring the electrical signal detected from below the lower leaflet surface and the electrical signal detected from above the upper leaflet surface.

In another aspect, provided herein is a method for tuning the sensing distance of the device, comprising: adjusting the ionic strength of an aqueous solution bounded by the functionalization layer and the lower leaflet surface of the lipid bilayer; and measuring the electrical signal detected from below the lower leaflet surface and the electrical signal detected from above the upper leaflet surface. In some embodiments, the ionic strength allows for differential analysis of an electrical signal arising from below the lower leaflet surface and an electrical signal arising from above the upper leaflet surface. In some of these embodiments, the differential analysis is sufficient to screen out the electrical signal detected from above the upper leaflet surface.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention. Provided also as embodiments of this disclosure are data figures that illustrate features by exemplification only, and not limitation.

Figure 4B:
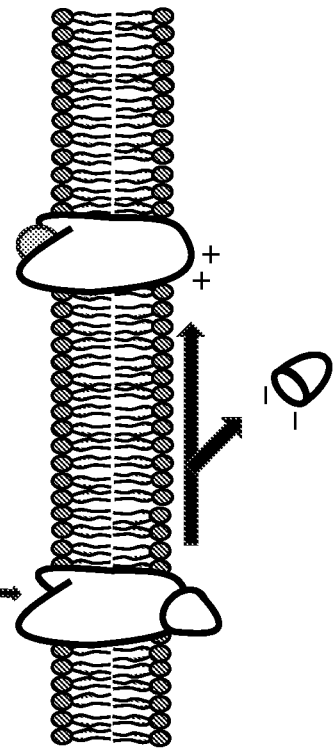
Figure 4A:
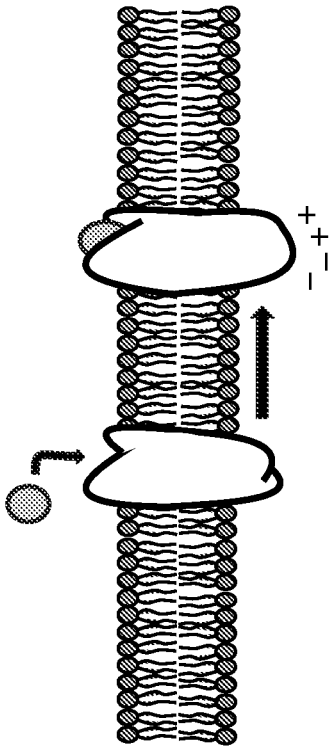
Figure 4D:
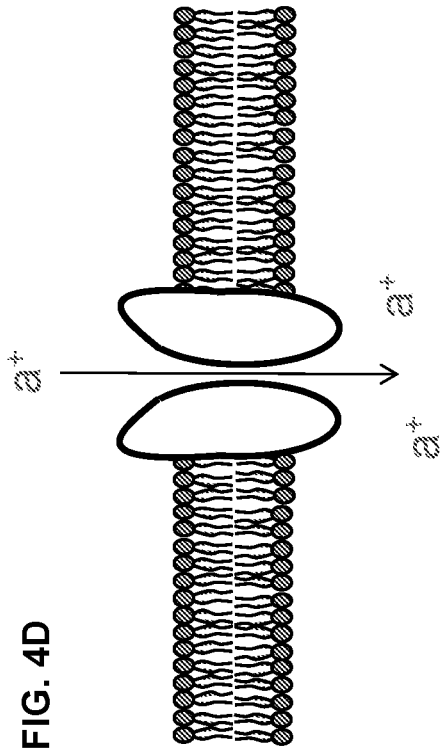
Figure 4C:
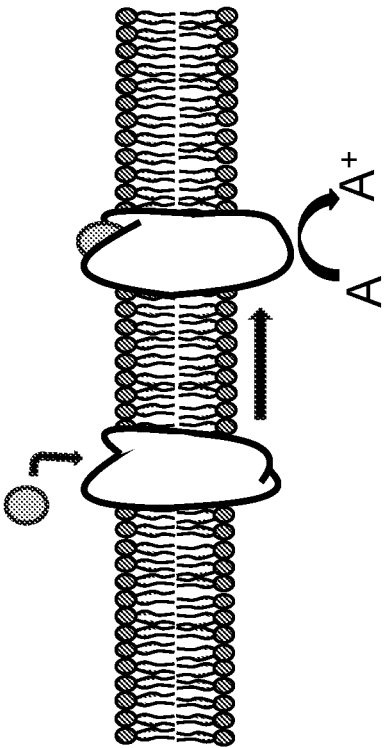

FIG. 4A, FIG. 4B, FIG. 4C, and FIG. 4D provide examples of detectable events induced by ligand binding or other stimuli, with FIG. 4A showing that a conformational change induced by ligand binding can result in net charge changes or charge rearrangements within the sensing space, FIG. 4B showing that dissociation or formation of a protein-protein interaction can lead to a net charge change or rearrangement of charges within the sensing space, FIG. 4C showing that ligand binding can lead to activation of an enzymatic activity which results in the generation of new ions and rearrangement of charges in the sensing space, and FIG. 4D showing that ligand binding or other stimuli can induce an ion channel or transporter to move charged species in either direction causing an increase or decrease of charged species within the sensing space.

Figure 5:
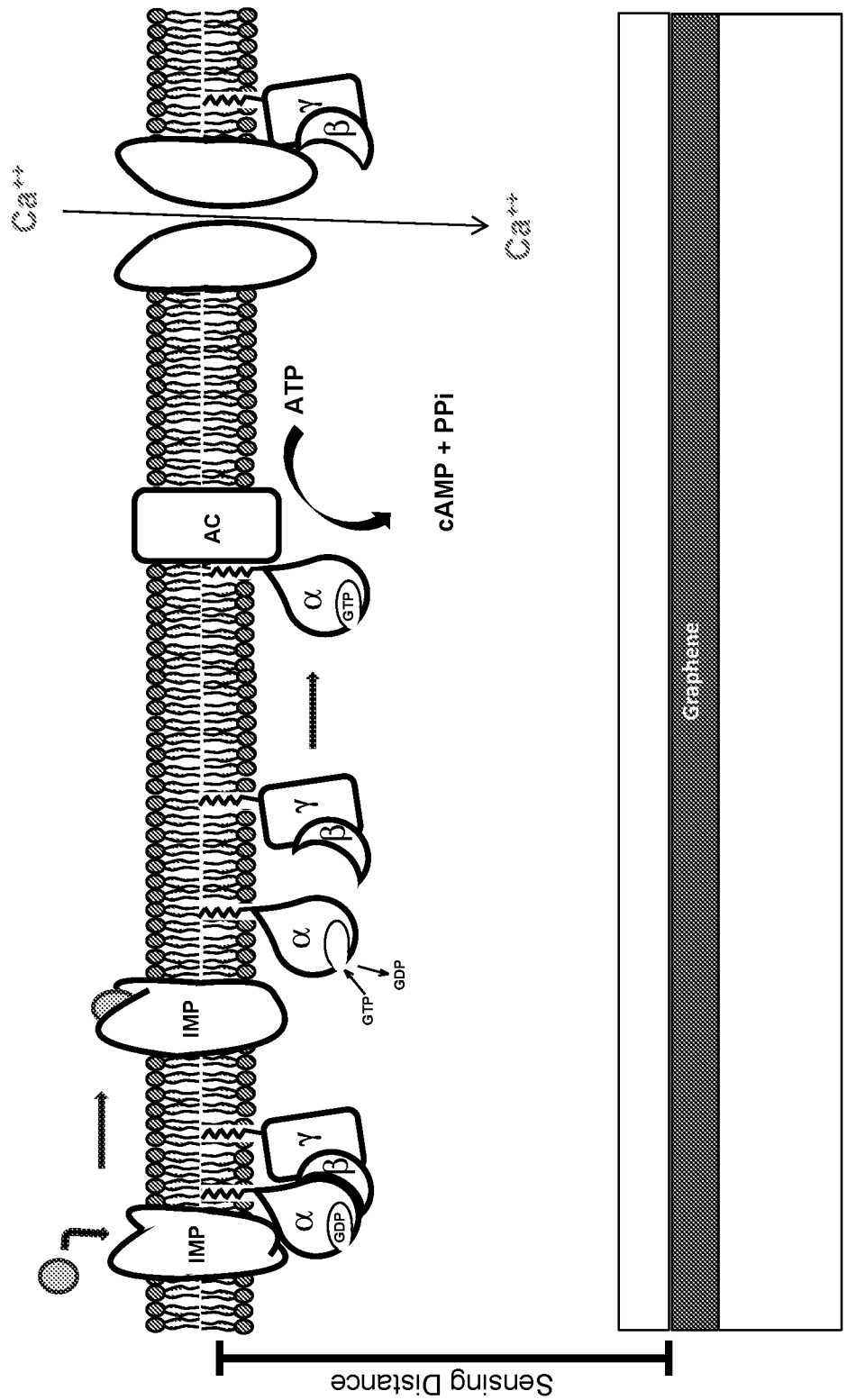

FIG. 5 illustrates that multiple detectable events can be induced by a single ligand binding event. A ligand binds to a G-protein-coupled receptor (GPCR) leading to a conformational change, which in turn induces G proteins to dissociate into subunits, release GDP and bind GTP. The G$\alpha$ subunit can activate adenylyl cyclase to produce cAMP and PPi from ATP. At the same time, the G$\beta\gamma$ dimer can activate $Ca^{++}$ channels causing influx of $Ca^{++}$ ions into the sensing space. Within the sensing space, each of these events can contribute to the signal by changing the net charge or charge distribution.

Figure 6:
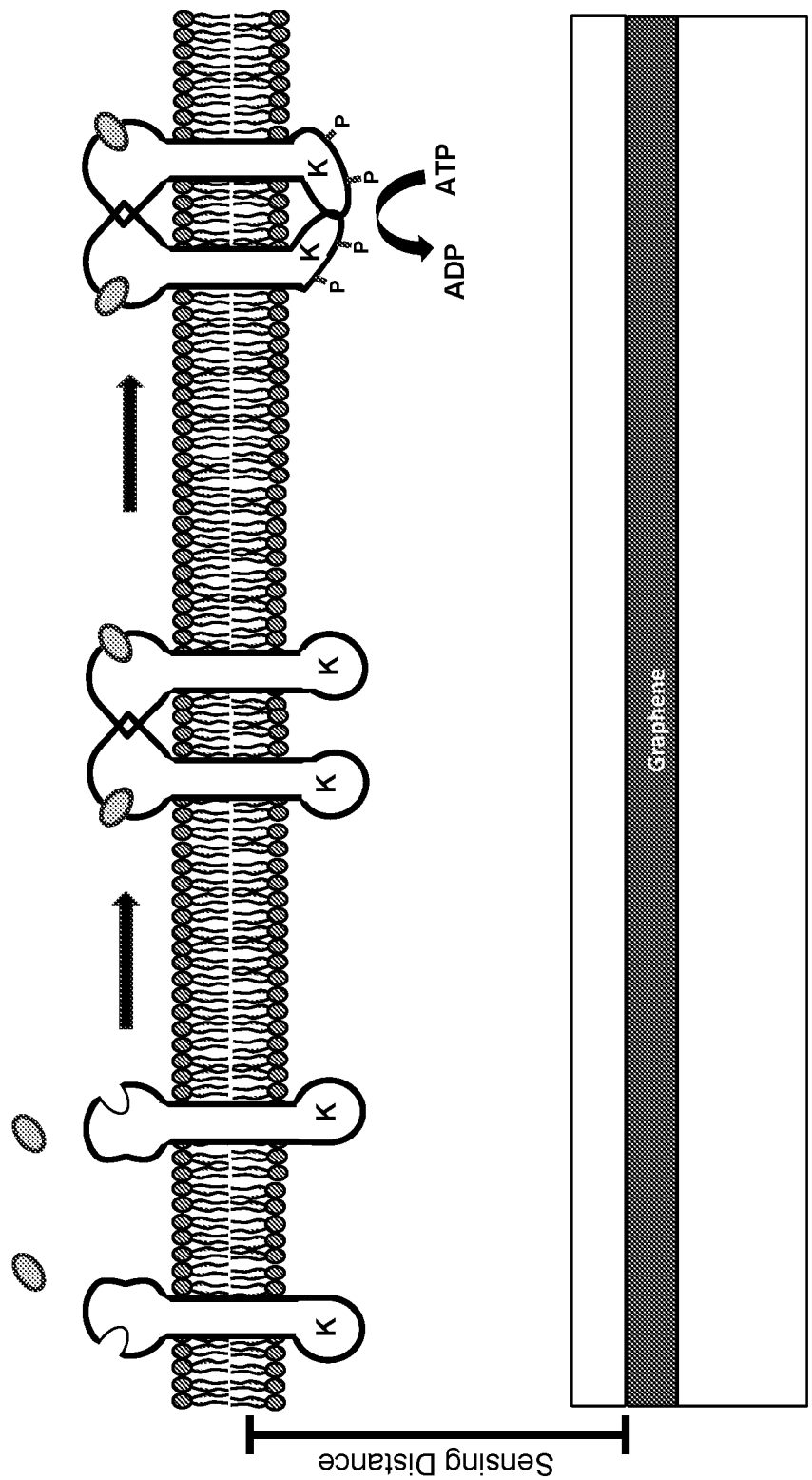

FIG. 6 illustrates the response of a receptor tyrosine kinase (RTK) such as the epidermal growth factor receptor (EGFR). Ligand binding to the receptor induces conformational changes that promote dimerization of the bound receptors, activation of the kinase domain, and phosphorylation of the intracellular domain. The phosphorylated domains are sites for protein binding for other signaling molecules. All events occurring within the sensing space can contribute to the signal by changing the net charge or charge distribution within the sensing space.

Figure 7:
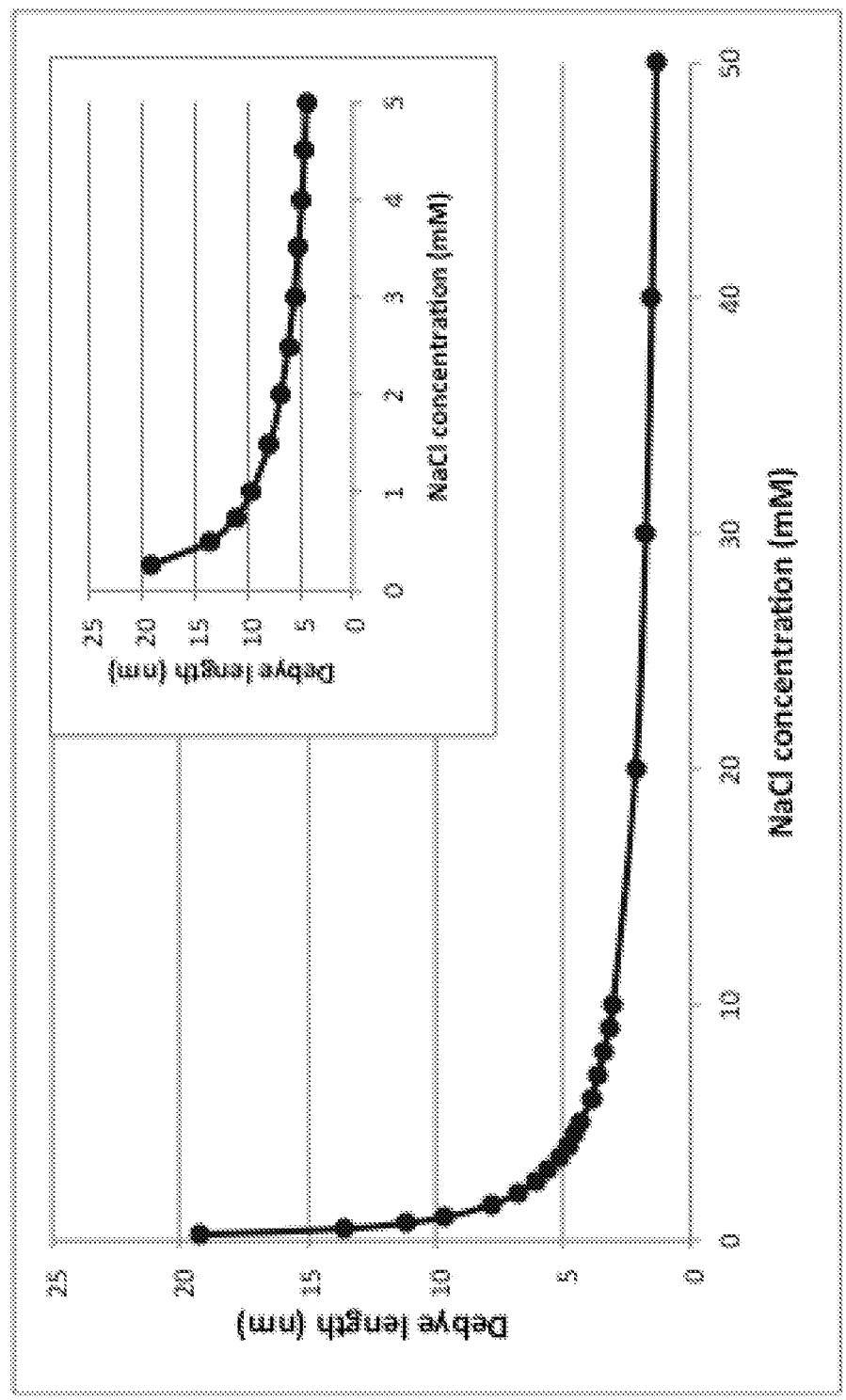

FIG. 7 provides a theoretical representation of the relationship between Debye length and the salt concentration of the aqueous buffer.

DETAILED DESCRIPTION

Throughout this application, the text refers to various embodiments of the present devices, compositions, systems, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure in their entireties.

As used herein, "support substrate" or "supporting substrate" refers to a substrate onto which the substrate insulating layer and the graphene layer can be deposited on. Nonlimiting examples of such substrates include: silicon, glass, quartz, mica, $SiO_2$, silicon/$SiO_2$, GaAs, GaN, polyethylene terephthalate (PET), and other polymer based materials.

As used herein, the term "substrate insulating layer" refers to an electrically insulating layer between the graphene layer and the support substrate. The substrate insulating layer materials comprise but are not limited to oxide materials that are at least 3 nm in thickness. In certain embodiments, when the support substrate is an insulating material, no substrate insulating layer is needed.

As used herein, "graphene layer" refers to a layer of carbon atoms, typically one, two, three, or four atoms thick. There are at least 100 carbon atoms in the graphene layer. Monolayer graphene refers to a graphene sheet that is one carbon atom thick for at least 50% of the area of the graphene layer.

As used herein, the term "functionalization layer" refers to a 1 nm-10 nm thin layer deposited or grown on the graphene sensor device to make the sensor device compatible with lipid bilayers and functional biochemistry. Examples of materials suitable for the functionalization layer include but are not limited to oxide, nitride, and oxinitride materials, such as $SiO_2$, $TiO_2$, $Al_2O_3$, $Ta_2O_5$, $Fe_3O_4$, $ZrO_2$, TiN, AlN, TiAlN, TiCN, $TiO_xN_y$, $SiO_xN_y$, SiN, and $Si_3N_4$. The functionalization layer can comprise solid state materials.

As used herein, the term "solid state material" refers a material that is formed from densely packed atoms with the property of a solid substance. Solid state materials include but are not limited to crystalline, polycrystalline, and amorphous solid material.

As used herein, the term "lipid bilayer" refers to a thin polar membrane made of two layers of lipid molecules. The cell membranes of almost all living organisms are made of lipid bilayer. Biological bilayers are usually composed of amphiphilic phospholipids that have a hydrophilic phosphate head and a hydrophobic tail consisting of two fatty acid chains. Biological membranes can also include cholesterol, proteins, and carbohydrates. In some embodiments, the lipid bilayer is a biological cell membrane with all its components, such as lipids, proteins, and oligosaccharides.

As used herein, "ionic strength" refers to a measure of the total concentration of ions in a solution. The ionic strength, I, of a solution is related to the charge and the concentration of each ion present in a solution and can be calculated by the following equation:

$$I = \frac{1}{2}\sum_{i=1}^{n} c_i z_i^2$$

where c is the molar concentration of ion i, and z is the charge number of ion i. Thus, the ionic strength of a solution can be adjusted by varying the concentration of salts and other charged species in a solution.

As used herein, "adjusting the ionic strength of an aqueous solution bounded by the functionalization layer and the lower leaflet surface of the lipid bilayer" includes adjusting the ionic strength of an aqueous solution that is present in at least the area bounded by the functionalization layer and the lower leaflet. In some embodiments, the aqueous solution can be present in additional regions besides the area bounded by the functionalization layer and the lower leaflet. In some embodiments, the aqueous solution completely covers the device.

As used herein, "electrode" refers to an electric conductor that is in electrical contact with the graphene layer. Nonlimiting examples of electrode materials include: gold, titanium, aluminum, copper, silver, platinum, palladium, and combinations thereof.

As used herein, the term "sensing distance" refers to the maximum distance from the graphene layer, at which an electrical signal can be detected by the device. Any changes in net charge or charge distribution occurring within the sensing distance are detectable by the device. Electrical signals at a distance larger than the sensing distance are weakly detected or not detected by the device. The sensing distance is variable because it is related to the type of ions present in the aqueous medium, the ionic strength of the aqueous medium, the Debye length, and the capacitance of the gating system. Therefore the sensing distance can be adjusted by a change in ionic strength of the aqueous medium. In some embodiments, measurements can be made at distances equivalent to as much as 100 times the Debye length. The sensing distance can be empirically determined or calculated. The sensing distance of the device described herein can vary from 0.5 nm to 100 nm, such as from 0.5 nm to 5 nm, from 0.5 nm to 10 nm, from 0.5 nm to 15 nm, from 0.5 nm to 20 nm, from 0.5 nm to 25 nm, from 0.5 nm to 30 nm, from 0.5 nm to 40 nm, from 0.5 nm to 50 nm, from 1 nm to 5 nm, from 1 nm to 10 nm, from 1 nm to 15 nm, from 1 nm to 20 nm, from 1 nm to 25 nm, from 1 nm to 30 nm, from 1 nm to 40 nm, from 1 nm to 50 nm, from 1 nm to 100 nm, from 2 nm to 5 nm, from 2 nm to 10 nm, from 2 nm to 15 nm, from 2 nm to 20 nm, from 2 nm to 25 nm, from 2 nm to 30 nm, from 2 nm to 40 nm, from 2 nm to 50 nm, from 2 nm to 100 nm, from 5 nm to 10 nm, from 5 nm to 15 nm, from 5 nm to 20 nm, from 5 nm to 30 nm, from 5 nm to 40 nm, from 5 nm to 50 nm, from 5 nm to 100 nm, from 10 nm to 15 nm, from 10 nm to 20 nm, from 10 nm to 30 nm, from 10 nm to 40 nm, from 10 nm to 50 nm, from 10 nm to 100 nm, from 15 nm to 20 nm, from 15 nm to 30 nm, from 15 nm to 40 nm, from 15 nm to 50 nm, from 15 nm to 100 nm, from 20 nm to 30 nm, from 20 nm to 40 nm, from 20 nm to 50 nm, from 20 nm to 100 nm, from 30 nm to 40 nm, from 30 nm to 50 nm, from 40 nm to 50 nm, from 40 nm to 100 nm, or from 50 nm to 100 nm.

As used herein, "spacer molecule" refers to a molecule positioned between the graphene sensor and the lipid bilayer to adjust the distance between the graphene surface and the upper surface of the lipid bilayer. In some embodiments, the distance between the graphene surface and the upper surface of the lipid bilayer is adjusted to be larger than the sensing distance of the biosensor, and the distance between the graphene surface and the lower surface of the lipid bilayer is equal or less than the sensing distance of the biosensor. Examples of spacer molecules include but are not limited to polymers such as proteins, polypeptides, and polyethylene glycols and nonpolymers, such as nanoparticles.

As used herein, "sensing space" refers to the space spanning from the surface of the graphene layer up to the sensing distance.

As used herein, the term "target molecule" refers to a biomolecule of interest that is embedded in the biological membrane, or is bound to the biological membrane layered on the surface of the functionalization layer. "Target molecule" also refers to a biomolecule of interest that can be conjugated to a functionalization molecule of the functionalization layer. Nonlimiting examples of target molecules include: a protein, a membrane protein, an integral membrane protein (IMP), a membrane associated protein, a glycoprotein, a phospholipid, and a glycolipid.

As used herein, the term "ligand" refers to a molecule that can bind to the target molecule. Nonlimiting examples of ligands include: an antibody, a hormone, a protein, a peptide, a nucleic acid, a polymer, a carbohydrate, a toxin, a neurotransmitter, a small molecule, a drug, a nanoparticle, a chemical compound, and an ion.

As used herein, the term "polymer" refers to a molecule or macromolecule composed of many repeated subunits. Nonlimiting examples of suitable polymers include: polypeptides, proteins, polyethylene glycol, nucleic acids such as DNA, RNA or synthetic analogs, polysaccharides, polyacrylates, cellulose, agarose, dextran, and any modified or substituted derivative of these polymers.

As used herein, the term "nanoparticle" refers to a particle between 1 and 100 nanometers in size. Suitable nanoparticles include, for example, silicon oxide and other metal oxide based nanoparticles.

As used herein, "membrane protein" refers to a protein that interacts with or is part of a biological membrane. Membrane proteins include integral membrane proteins and peripheral membrane proteins.

As used herein, "peripheral membrane protein" refers to a membrane protein that adheres temporarily to the biological membrane with which it is associated. Peripheral membrane proteins can attach to integral membrane proteins, or insert into the peripheral region of the lipid bilayer. Nonlimiting examples of peripheral membrane proteins include regulatory protein subunits of ion channels, regulatory protein subunits of transmembrane receptors, and GPI anchored proteins.

As used herein, "integral membrane protein (IMP)" refers to a membrane protein that is permanently attached to the biological membrane. The most common type of IMP is transmembrane protein (TM), which spans the entire biological membrane. Integral monotopic proteins are associated to the membrane from one side but do not span the lipid bilayer completely.

As used herein, the term "native state" refers to a properly folded and/or assembled form of biomolecule. The native state of a biomolecule can possess all four levels of biomolecular structure, with the secondary through quaternary structure being formed from weak interactions along the covalently-bonded backbone. The native state is in contrast to the denatured state, in which the weak interactions are disrupted, such as by detergent treatment, leading to the loss of one or more higher orders of structure such as the secondary, tertiary, and/or quaternary structure while retaining the biomolecule's primary structure.

As used herein, the term "agonist" refers to a ligand that binds to a receptor and activates the receptor to produce a certain biological response. Receptors can be activated by either endogenous or exogenous agonists. An endogenous agonist is a compound naturally produced by the body that binds and activates a particular receptor. Nonlimiting examples of endogenous agonists include hormones and neurotransmitters. Nonlimiting examples of exogenous agonists include drugs.

As used herein the term "inverse agonist" refers to a ligand that induces a receptor to produce a response that is opposite to the response induced by an agonist.

As used herein, the term "antagonist" refers to a ligand that blocks or dampens the agonist-mediated response of a receptor rather than provoking a biological response itself upon binding to a receptor. Many drug antagonists achieve their potency by competing with endogenous ligands or substrates at structurally defined binding sites on the receptors. Nonlimiting examples of antagonists include alpha blockers, beta blockers, and calcium channel blockers.

As used herein, the term "inactive ligand" refers to a ligand that is neither an agonist nor an antagonist. Inactive ligand has no effect on the receptor directly or indirectly.

As used herein, the term "differential analysis" refers to any analysis for distinguishing the signal at or above the top of the membrane from the signal at or below the bottom of the membrane.

As used herein, the term "screen out" refers to a process of correcting the signal at or above the top of the membrane to the minimum.

As used herein, "$K_d$" or "$K_D$" refers to "dissociation constant," which is a specific type of equilibrium constant that measures the propensity of a larger object to separate (dissociate) reversibly into smaller components, as when a complex falls apart into its component molecules. The dissociation constant is the inverse of the association constant. For a general reaction $$A_xB_y \rightleftharpoons xA + yB$$

in which a complex $A_xB_y$ breaks down into x A subunits and y B subunits, the dissociation constant is defined $$K_d = \frac{[A]^x \times [B]^y}{[A_xB_y]}$$

where [A], [B], and [$A_xB_y$] are the concentrations of A, B, and the complex $A_xB_y$, respectively.

Graphene Bio-Electronic Sensing

Because of its high sensitivity and selectivity, graphene field effect transistors (GFETs) present ideal tools for sensing applications. When a ligand molecule binds to a target molecule on the graphene surface, the redistribution of electronic charge generates a change in the electric field across the graphene field effect transistor (GFET), which changes the electronic conductivity and device response. The detection of the binding event is accomplished by measuring the current and the current change of GFET.

A graphene field effect transistor (GFET) comprises a source electrode, a drain electrode, a gate, and a graphene channel region connecting the source and the drain electrodes. Graphene layer can be modified with biomolecule conjugates, which anchor biomolecules to the surface of the graphene layer. In some embodiments, the target biomolecule contains specific groups that can be recognized by a ligand molecule. The binding of the ligand molecule to the target molecule is detected by measuring the current change.

The surface of the GFET channel can be functionalized with proteins, chemical compounds, and DNA molecules to make sensors for various applications.

In some embodiments, a lipid bilayer containing a target molecule is layered on the graphene layer or on the functionalization layer and binding of ligands to the target molecule is detected by current changes. In some embodiments, a spacer molecule is positioned between the graphene sensor and the lipid bilayer containing a target molecule.

Measurement of IMP Function

Many integral membrane proteins (IMPs) are transmembrane proteins that typically have hydrophilic domains exposed or protruding on one or both sides of the lipid bilayer. The binding of a ligand, or other stimuli, to an IMP site on one side of the lipid bilayer typically induces a conformational change on the IMP. This conformational change can include a conformational change in the domain exposed on the other side of the lipid bilayer. Thus, ligand binding to the IMP on one side of the lipid bilayer sends a signal, such as a conformational change, to the other side of the lipid bilayer. This is known as signal transduction. This conformational change can in turn, induce a variety of downstream responses initiating a chain of events that eventually result in regulation of cellular homeostasis. In some embodiments, the ligand-induced conformational changes cause the IMP to dimerize by interacting with another ligand bound IMP. This dimerization in turn can elicit a number of responses on the other side of the lipid bilayer.

The graphene biosensor described herein can detect net charge changes and charge distribution changes occurring within a certain distance from the graphene layer. This distance is the sensing distance of the device. The space spanning from the graphene layer surface up to the sensing distance is the sensing space. Events occurring at a distance beyond the sensing distance, outside the sensing space, will not be detected or will only be weakly detectable. The device described herein can test a ligand's ability to modulate IMP function (i.e. signal transduction) by measuring ligand-induced net charge or charge distribution changes within the sensing space. Examples of detectable ligand-induced changes include conformational changes and a variety of responses such as protein-protein interactions, enzymatic reactions, transport of ions and metabolites, and other events causing a change in net charge or charge distribution within the sensing space.

Figure 1B:
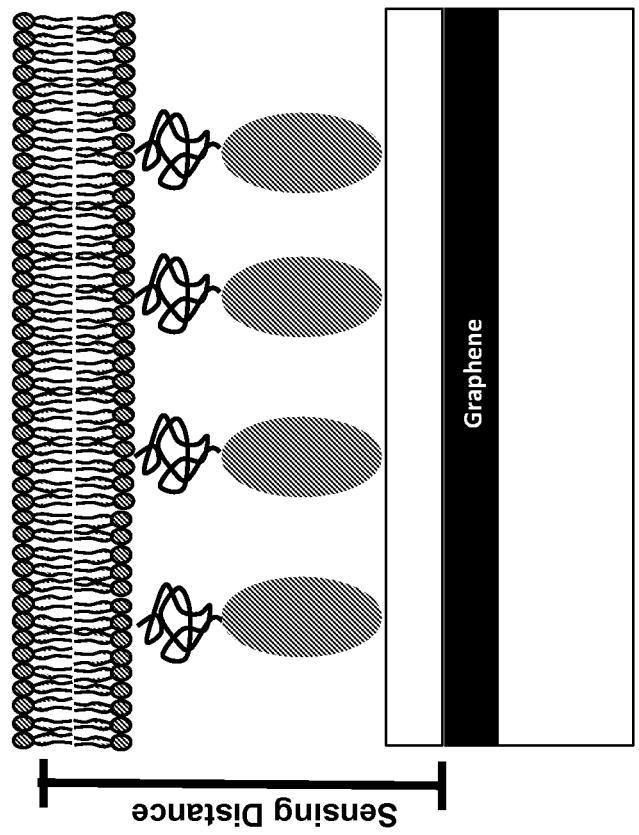
FIG. 1A and FIG. 1B show a comparison between the control design and the raised design, with FIG. 1A presenting the control design which can detect events above and below the membrane, and FIG. 1B representing the raised design with which only events below the membrane are detectable.
Figure 1A:
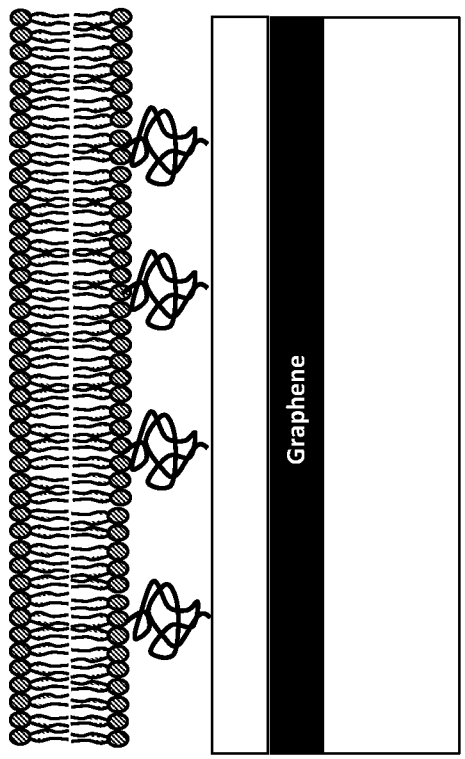

As described herein, spacer molecules such as proteins or polymers are positioned between the graphene biosensor and the lipid bilayer such that the upper surface of the lipid bilayer is at or beyond the sensing distance of the device. In this configuration, the ligand binding to the upper surface of the lipid bilayer will not be detected. However, ligand-induced events representing IMP function that occur within the sensing space will be detected (FIG. 1A and FIG. 1B). In some embodiments, the lower surface of the lipid bilayer is at or within the sensing distance. In some embodiments, the lower surface of the lipid bilayer is beyond the sensing distance. In some embodiments, the spacer molecules are attached to the graphene layer. In some embodiments, the spacer molecules are attached to the functionalization layer. In some embodiments, the spacer molecules are attached to the lower leaflet of the lipid bilayer. In some embodiments, the spacer molecules are attached to the hydrophobic interior volume of the lipid bilayer. In some embodiments, the spacer molecules are attached to the upper leaflet of the lipid bilayer.

Using the device described herein, the function of an IMP can be measured. In some embodiments, the function of the IMP can be measured by a change in net charge within the sensing space. In some embodiments, the function of the IMP can be measured by a change in charge distribution within the sensing space. In certain embodiments, the function of the IMP directly causes the change in net charge or charge distribution within the sensing space. In certain other embodiments, the function of the IMP indirectly causes the change in net charge or charge distribution within the sensing space.

Device

Figure 2:
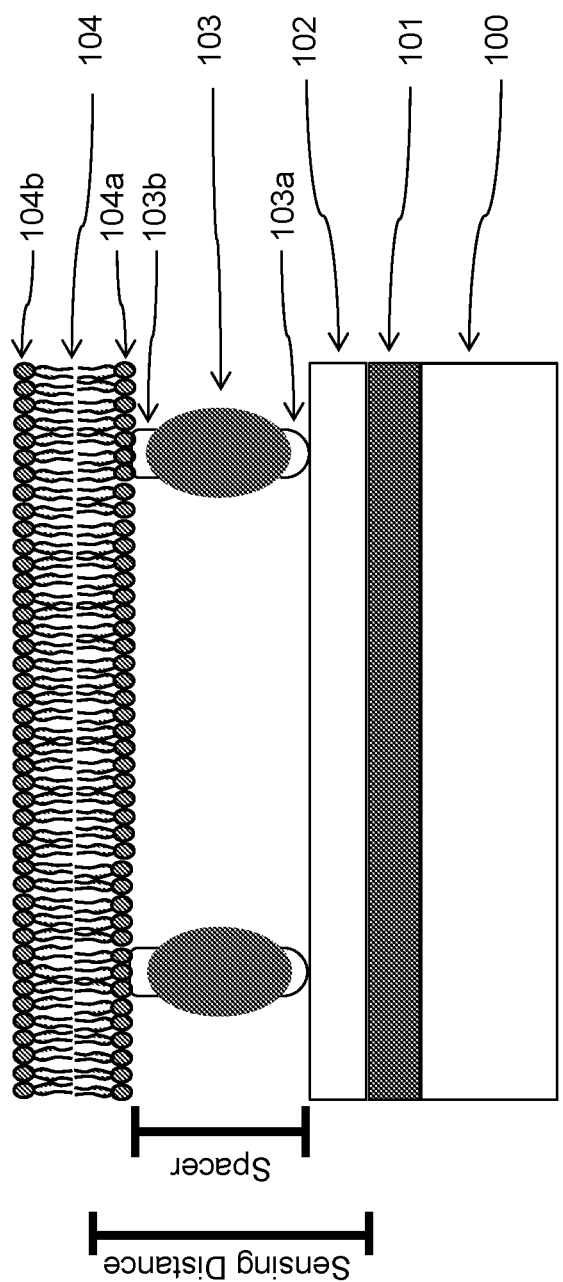
FIG. 2 provides a detailed depiction of the components of the raised design where spacer molecules are positioned between the functionalization layer and the lower leaflet of the lipid bilayer such that the distance between the graphene surface and the upper leaflet of the lipid bilayer is greater than the sensing distance, with 100 representing the support substrate, 101 representing the graphene layer, 102 representing the functionalization layer, 103 representing the spacer molecule, 103a representing the first binding moiety of the spacer molecule, 103b representing the second binding moiety of the spacer molecule, 104 representing the lipid bilayer, 104a representing the lower leaflet of the lipid bilayer, and 104b representing the upper leaflet of the lipid bilayer.

Aspects of the subject disclosure include graphene sensor devices that comprise a support substrate, a graphene layer, electrodes, a functionalization layer, a spacer molecule, a lipid bilayer, and optionally a substrate insulating layer (FIG. 2).

Support Substrate

Support substrate refers to a substrate onto which the insulating layer and the graphene layer can be deposited. In various embodiments, the support substrate is used to support graphene sensor devices. Nonlimiting examples of such substrates include: silicon, glass, quartz, $SiO_2$, silicon/$SiO_2$, GaAs, GaN, polyethylene terephthalate (PET), and other polymer based materials. In some embodiments, the support substrate comprises silicon or $SiO_2$. In certain embodiments, the support substrate comprises silicon. In some embodiments, the support substrate is a semiconducting substrate. In some other embodiments, the support substrate is an insulating substrate. In various embodiments, the thickness of the support substrate is from about 5 μm to about 10000 μm, such as about 10 μm to about 5000 μm, about 50 μm to about 2500 μm, or about 100 μm to about 1000 μm.

Substrate Insulating Layer

Substrate insulating layer refers to an electrically insulating layer between the graphene layer and the support substrate. In various embodiments, the substrate insulating layer is deposited on the support substrate. In various embodiments, the graphene layer is placed directly onto the substrate insulating layer on the support substrate. In some embodiments, the substrate insulating layer comprises an oxide material. In some of these embodiments, the oxide of the substrate insulating layer is selected from the group consisting of: $SiO_2$, $TiO_2$, $Al_2O_3$, $Ta_2O_5$, $Fe_3O_4$, and $ZrO_2$. In some other embodiments, the substrate insulating layer comprises a nitride material. In various embodiments, the substrate insulating layer is at least 3 nm in thickness, such as at least 5 nm, at least 10 nm, at least 50 nm, or at least 100 nm in thickness. In some embodiments, the substrate insulating layer is about 3 nm to about 100000 nm in thickness, such about 5 nm to about 50000 nm, about 10 nm to about 10000 nm, or about 100 nm to about 1000 nm in thickness. In certain preferred embodiments, the substrate insulating layer is a 100 nm to 300 nm thick layer of thermally grown $SiO_2$. In various embodiments, the substrate insulating layer has a dielectric constant of 1 to 100, such as 2 to 80, 5 to 60, 10 to 50, or 20 to 40. In certain embodiments, when the support substrate is an insulating material, no substrate insulating layer is needed.

Graphene Layer

Graphene layer refers to a layer of carbon atoms, typically one, two, three, or four atoms thick. In various embodiments there are at least 100 carbon atoms in the graphene substrate, such as at least 200 carbon atoms, at least 500 carbon atoms, or at least 1000 carbon atoms. In certain embodiments, the graphene layer is a graphene monolayer. In some embodiments, the graphene monolayer is one carbon atom thick for at least 50% of the area of the graphene layer.

In various embodiments, the graphene layer is transferred onto the support substrate and placed directly onto the insulating layer. In some embodiments, the electrodes are deposited on top of the graphene layer. In some other embodiments, the graphene layer is deposited on top of the electrodes.

In some embodiments, the graphene layer is unpatterned. In some other embodiments, the graphene layer is patterned. In some of these embodiments, the graphene layer is patterned using standard photolithography methods. In some embodiments, the standard photolithography methods comprise spincoating positive i-Line resist onto the graphene substrate to about 1.3 μm thickness, exposing, and chemically developing the positive i-Line resist to create resist/graphene features. In certain embodiments, the resist/graphene features are 1 μm×1 μm, 2 μm×2 μm, 5 μm×5 μm, 10 μm×10 μm, 20 μm×20 μm, 40 μm×40 μm, 80 μm×80 μm, or 100 μm×100 μm in area. In some embodiments, graphene features as small as 90 nm across can be obtained using immersion photolithography. In some embodiments, graphene features as small as 10 nm across can be achieved using electron beam lithography methods. In various embodiments, an $O_2$ RIE plasma etching system is used to etch away the graphene exposed by lithography. In some embodiments, a resist stripper solution is used to remove the protective resist covering the patterned graphene features. In some of these embodiments, the resist stripper solution is microposit 1165 or PRS3000.

Electrodes

Electrode refers to the electrical conductor that is electrically connected to the graphene layer. In some embodiments, the electrodes are deposited on top of the graphene layer. In some other embodiments, the graphene layer is deposited on top of the electrodes. In certain embodiments, after the graphene features are patterned, standard semiconductor processing techniques are used to generate the pattern for electrodes, with subsequent metal deposition and lift-off to expose the desired electrode pattern above the graphene pattern. In certain other embodiments, the electrodes are patterned first, and the graphene layer is transferred on top of the electrodes and subsequently patterned. In some embodiments, the electrode is deposited by thermal evaporation. In some embodiments, the excess electrode material is removed using a standard lift-off step.

In various embodiments, the electrode materials comprise metals such as gold, titanium, aluminum, copper, silver, platinum, palladium, and combinations thereof. In some embodiments, the electrode materials are titanium and gold. In some of these embodiments, titanium is used as an adhesion layer for gold. In various embodiments, the electrodes are about 10 nm to about 1000 nm in thickness, such as about 20 nm to about 800 nm, about 30 nm to about 500 nm, or about 40 nm to about 300 nm in thickness. In certain preferred embodiments, the electrodes are about 40 nm in thickness. In various embodiments, the electrodes are about 1 μm to about 100 μm in width, such as about 2 μm to about 80 μm, about 5 μm to about 40 μm, or about 10 μm to about 20 μm in width. In some preferred embodiment, the electrodes are about 10 μm to about 20 μm in width.

In some embodiments, the electrode comprises a source and a drain. In some embodiments, the electrode further comprises a gate. In some embodiments, the electrode is in electrical contact with the graphene layer. In some embodiments, the electrode is connected to an electrical power supply configured to generate an electrical potential on the graphene layer. In some embodiments, the electrode is configured to measure a current or a change in current through the graphene layer.

Functionalization Layer

Functionalization layer refers to a layer deposited or grown on the graphene sensor device to make the sensor device compatible with lipid bilayers and functional biochemistry. In various embodiments, the functionalization layer protects the sensing surface from ambient contamination and allows lipid bilayer assembly or chemical conjugation above the surface. In some embodiments, the thickness of the functionalization layer varies from about 1 nm to about 50 nm, such as about 1 nm to about 20 nm, about 1 nm to about 10 nm, about 1 nm to about 5 nm. In some of these embodiments, the thickness of the functionalization layer is from about 1 nm to about 3 nm. In certain embodiments, the thickness of the functionalization layer is less than 10 nm, such as less than 9 nm, less than 8 nm, less than 7 nm, less than 6 nm, less than 5 nm, less than 4 nm, less than 3 nm, or less than 2 nm.

In various embodiments, the functionalization layer comprises solid state material deposited continuously on the graphene layer. In some embodiments, the solid state material can be crystalline, polycrystalline, or amorphous solid material. In some embodiments, the functionalization layer provides a continuous hydrophilic surface on top of the graphene layer, allowing the formation of a biological membrane on the surface. In various embodiments, the thickness of the functionalization layer can be adjusted to allow the optimal formation of the biological membrane and the fine-tuning of the device. In some embodiments, the functionalization layer protects the graphene layer from external contamination and keep the graphene layer intact.

In various embodiments, the material for the functionalization layer is electrically insulating such that it does not short the sensor. In various embodiments, the materials for the functionalization layer can be oxide, nitride and oxinitride materials. In certain embodiments, the functionalization layer comprises an oxide. In some of these embodiments, the oxide can be $SiO_2$, $TiO_2$, $Al_2O_3$, $Ta_2O_5$, $Fe_3O_4$, or $ZrO_2$. In certain embodiments, the functionalization layer comprises a nitride or an oxinitride. In some of these embodiments, the nitride or oxinitride can be TiN, AlN, TiAlN, TiCN, $TiO_xN_y$, $SiO_xN_y$, SiN, or $Si_3N_4$. In certain preferred embodiments, the material for the functionalization layer is $SiO_2$.

In some embodiments, the functionalization layer has a dielectric constant in the range of 1 to 100, such as 2 to 80, 5 to 60, 10 to 50, or 20 to 40. In some embodiments, the product of the dielectric constant and the thickness of the functionalization layer is less than 1000 nm, such as less than 100 nm, less than 10 nm, or less than 1 nm.

In various embodiments, the functionalization layer comprises a functionalization molecule. In some of these embodiments, the functionalization molecule comprises silane. In various embodiments, the silane can be 3-aminopropyltrimethoxysilane (APTMS, amino), 3-aminoproplyltriethoxysilane (APTES, amino), 3-isocyanatopropyltriethoxysilane (CYNPS, isocyanate), triethoxysilylbutyraldehyde (ALDPS, aldehyde), (3-glycidoxypropyl) trimethoxysilane (GPS, epoxy), 3-mercaptopropyltrimethoxysilane (MPS, sulfur), 7-octenyltrimethoxysilane (OTS, vinyl), 3-methacryloxypropyltrimethoxysilane (acrylate), 3,4-epoxycyclohexyltrimethoxysilane (ECPS, epoxy), 10-undecenyltrichlorosilane (V11TCS, vinyl), or carboxylethylsilanetriol. In some embodiments, the functionalization layer further comprises a reactive group, such as a carboxyl group, a hydroxyl group, an amine group, an epoxy group, an aldehyde group, a sulfhydryl group, or other reactive groups used in surface chemistry methods well known to those skilled in the arts. In various embodiments, the reactive group is covalently bound to a functionalization molecule. In certain embodiments, the carboxyl group is covalently bound to a functionalization molecule. In certain embodiments, the hydroxyl group is covalently bound to a functionalization molecule. In some embodiments, the thickness of the functionalization molecule varies 1 nm to 50 nm, such as 2 nm to 20 nm, or 5 nm to 10 nm.

The deposition of the functionalization layer can be done via physical/thermal deposition or via chemical methods. In some embodiments, the physical/thermal deposition is e-beam evaporation. In some embodiments, the chemical deposition is atomic layer deposition. In certain embodiments, when the electrodes are deposited on top of the graphene layer, the functionalization layer is deposited on top of both the electrodes and the graphene layer. In certain other embodiments, when the graphene layer is deposited on top of the electrodes, the functionalization layer is deposited on top of the graphene layer.

Spacer Molecule

Spacer molecule refers to a molecule positioned between the graphene sensor and the lipid bilayer such that the distance between the graphene sensor and the upper surface of the lipid bilayer is modulated. In some embodiments, the spacer molecule is attached to the functionalization layer. In some embodiments, the spacer molecule is attached to the graphene layer. In some embodiments, the spacer molecule is attached to the lower leaflet of the lipid bilayer. In some embodiments, the spacer molecule is attached to the hydrophobic interior volume of the lipid bilayer. In some embodiments, the spacer molecule is attached to the upper leaflet of the lipid bilayer. In some embodiments, the distance between the graphene sensor and the upper surface of the lipid bilayer is larger than the sensing distance of the device. In some embodiments, the distance between the graphene layer and the upper surface of the lipid bilayer is equal to the sensing distance of the device. In some embodiments, the distance between the graphene layer and the upper surface of the lipid bilayer is smaller than the sensing distance of the device.

In some embodiments, the spacer molecule comprises a first binding moiety and a second binding moiety. In certain embodiments, the first binding moiety is attached to the functionalization layer. In certain embodiments, the first binding moiety is attached to the graphene layer. In certain embodiments, the second binding moiety is attached to the lower leaflet surface of the lipid bilayer. In certain embodiments, the second binding moiety is attached to the hydrophobic interior volume of the lipid bilayer. In certain embodiments, the second binding moiety is attached to the upper leaflet surface of the lipid bilayer. The attachment can be covalent or non-covalent.

A spacer molecule can be any molecule whose size allows the desired distance between the upper surface of the lipid bilayer and the graphene layer. Non-limiting examples of spacer molecules include polymers such as peptides, polypeptides, proteins such as BSA, nucleic acids, polyethylene glycol, polyacrylates, celluloses, polysaccharides, agarose, dextran, and modified or substituted derivatives of any of these polymers or combinations thereof.

In certain embodiments, the spacer molecule comprises a chemical linker. In certain embodiments, the spacer molecule comprises a nanoparticle. In certain embodiments, the spacer molecule is covalently linked to the functionalization layer. In certain embodiments, the spacer molecule is non-covalently linked to the functionalization layer. In certain embodiments, the spacer molecule is covalently linked to the graphene layer. In certain embodiments, the spacer molecule is non-covalently linked to the graphene layer.

In some embodiments, the spacer molecule is a covalently immobilized maleic acid copolymer, an anchor molecule such as HC18 (Z-20-(Z-octadec-9-enyloxy)-3,6,9,12,15,18, 22-heptaoxatetracont-31-ene-1-thiol), a Silane PEG-lipid, a DNA-lipid, an avidin/biotynylated lipid, Poly-L-Lysine, an immobilized/tethered cholesterol, or a DNA-cholesterol. In some embodiments, the spacer molecule is a silane. In various embodiments, the silane can be 3-aminopropyltrimethoxysilane (APTMS, amino), 3-aminoproplyltriethoxysilane (APTES, amino), 3-isocyanatopropyltriethoxysilane (CYNPS, isocyanate), triethoxysilylbutyraldehyde (AL- DPS, aldehyde), (3-glycidoxypropyl) trimethoxysilane (GPS, epoxy), 3-mercaptopropyltrimethoxysilane (MPS, sulfur), 7-octenyltrimethoxysilane (OTS, vinyl), 3-methacryloxypropyltrimethoxysilane (acrylate), 3,4-epoxycyclohexyltrimethoxysilane (ECPS, epoxy), 10-undecenyltrichlorosilane (V11TCS, vinyl), or carboxylethylsilanetriol.

In certain embodiments, the spacer molecule comprises a polyethylene glycol. In various embodiments, the molecular weight of the polyethylene glycol ranges from 500 Dalton to 100,000 Dalton, such as from 500 Dalton to 1,000 Dalton, from 500 Dalton to 2,000 Dalton, from 500 Dalton to 3,000 Dalton, from 500 Dalton to 4,000 Dalton, from 500 Dalton to 5,000 Dalton, from 500 Dalton to 10,000 Dalton, from 500 Dalton to 20,000 Dalton, from 500 Dalton to 30,000 Dalton, from 500 Dalton to 40,000 Dalton, from 500 Dalton to 50,000 Dalton, from 1,000 Dalton to 2,000 Dalton, from 1,000 Dalton to 3,000 Dalton, from 1,000 Dalton to 4,000 Dalton, from 1,000 Dalton to 5,000 Dalton, from 1,000 Dalton to 10,000 Dalton, from 1,000 Dalton to 20,000 Dalton, from 1,000 Dalton to 30,000 Dalton, from 1,000 Dalton to 40,000 Dalton, from 1,000 Dalton to 50,000 Dalton, from 1,000 Dalton to 100,000 Dalton, from 2,000 Dalton to 3,000 Dalton, from 2,000 Dalton to 4,000 Dalton, from 2,000 Dalton to 5,000 Dalton, from 2,000 Dalton to 10,000 Dalton, from 2,000 Dalton to 20,000 Dalton, from 2,000 Dalton to 30,000 Dalton, from 2,000 Dalton to 40,000 Dalton, from 2,000 Dalton to 50,000 Dalton, from 2,000 Dalton to 100,000 Dalton, from 3,000 Dalton to 4,000 Dalton, from 3,000 Dalton to 5,000 Dalton, from 3,000 Dalton to 10,000 Dalton, from 3,000 Dalton to 20,000 Dalton, from 3,000 Dalton to 30,000 Dalton, from 3,000 Dalton to 40,000 Dalton, from 3,000 Dalton to 50,000 Dalton, from 3,000 Dalton to 100,000 Dalton, from 4,000 Dalton to 5,000 Dalton, from 4,000 Dalton to 10,000 Dalton, from 4,000 Dalton to 20,000 Dalton, from 4,000 Dalton to 30,000 Dalton, from 4,000 Dalton to 40,000 Dalton, from 4,000 Dalton to 50,000 Dalton, from 4,000 Dalton to 100,000 Dalton, from 5,000 Dalton to 10,000 Dalton, from 5,000 Dalton to 20,000 Dalton, from 5,000 Dalton to 30,000 Dalton, from 5,000 Dalton to 40,000 Dalton, from 5,000 Dalton to 50,000 Dalton, from 5,000 Dalton to 100,000 Dalton, from 10,000 Dalton to 20,000 Dalton, from 10,000 Dalton to 30,000 Dalton, from 10,000 Dalton to 40,000 Dalton, from 10,000 Dalton to 50,000 Dalton, from 10,000 Dalton to 100,000 Dalton, from 20,000 Dalton to 50,000 Dalton, from 20,000 Dalton to 100,000 Dalton, or from 50,000 Dalton to 100,000 Dalton.

In some embodiments, the spacer molecule comprises one or more polypeptides or proteins such as streptavidin (5 nm), BSA (7 nm), IgG (15 nm), IgM (35 nm), or other polypeptide or protein with an average radius between 1 nm and 50 nm, such as between 1 nm and 5 nm, between 1 nm and 10 nm, between 1 nm and 20 nm, between 1 nm and 30 nm, between 1 nm and 40 nm, between 5 nm and 10 nm, between 5 nm and 20 nm, between 5 nm and 30 nm, between 5 nm and 40 nm, between 5 nm to 50 nm, between 10 nm and 20 nm, between 10 nm and 30 nm, between 10 nm and 40 nm, between 10 nm to 50 nm, between 20 nm and 30 nm, between 20 nm and 40 nm, between 20 nm to 50 nm, between 30 nm and 40 nm, between 30 nm to 50 nm, or between 40 nm to 50 nm. In various embodiments, the molecular weight of the polypeptide or protein ranges from 500 Dalton to 1,000,000 Dalton, such as from 500 Dalton to 1,000 Dalton, from 500 Dalton to 10,000 Dalton, from 500 Dalton to 50,000 Dalton, from 500 Dalton to 100,000 Dalton, from 500 Dalton to 500,000 Dalton, from 1,000 Dalton to 10,000 Dalton, from 1,000 Dalton to 50,000 Dalton, from 1,000 Dalton to 100,000 Dalton, from 1,000 Dalton to 500,000 Dalton, from 1,000 Dalton to 1,000,000 Dalton, from 10,000 Dalton to 50,000 Dalton, from 10,000 Dalton to 100,000 Dalton, from 10,000 Dalton to 500,000 Dalton, from 10,000 Dalton to 1,000,000 Dalton, from 50,000 Dalton to 100,000 Dalton, from 50,000 Dalton to 500,000 Dalton, from 50,000 Dalton to 1,000,000 Dalton, from 100,000 Dalton to 500,000 Dalton, from 100,000 Dalton to 1,000,000 Dalton, or from 500,000 Dalton to 1,000,000 Dalton.

In some embodiments, nanoparticles of suitable size can also be used as spacer molecules. For example, silicon oxide and other metal oxide based nanoparticles.

In some embodiments, a single kind of spacer molecule is used. In some embodiments, a combination of two or more spacer molecules is used. In some embodiments, two or more spacer molecules can be stacked in layers to achieve a higher spacing between the graphene and the lower leaflet surface.

Lipid Bilayer

In various embodiments, the device comprises a lipid bilayer with an upper leaflet surface, a lower leaflet surface and a hydrophobic interior volume bounded by the upper leaflet and the lower leaflet surfaces.

The lipid bilayer can be composed of any phospholipid or bilayer membrane component such as, but not limited to: phosphoethanolamines, phosphocholines phosphotidylserines with saturated and unsaturated tails of any length, cardiolipid, cholesterol and its derivatives such as ergosterol, epicholesterol, sphingomyelin, carbohydrates. The lipid bilayer can also contain other polymeric amphiphilic components.

In some embodiments, the lipid bilayer is a cushioned lipid bilayer prepared by methods well known to those skilled in the arts. Briefly, proteoliposomes or native cell membrane vesicles (NMVs), and small unilamellar vesicles (SUVs) containing, for example, 0.1-5% PEG-PE and 99.9-95% POPC, are prepared using methods well known in the art. In some embodiments, PEG-PE is a spacer molecule incorporated into the lipid bilayer of SUVs. The functionalization layer is cleaned by RIE. Then, proteoliposomes or cell membrane vesicles in PBS buffer are exposed to the sensor surface for up to 30 min. Unbound proteoliposomes or NMVs are then washed away by gentle flow. The surface is then incubated with SUVs in PBS buffer containing 5-20 mM EDTA for at least 20 min. Excess SUVs are washed by gentle flow. In certain embodiments, the fluidity of the resulting lipid bilayer is measured by fluorescence recovery after photobleaching (FRAP) assay.

In various embodiments, the biological membrane is in native state. In some embodiments, the preparation of biological membrane does not involve disruptive steps, such as detergent solubilization and reconstitution. In some embodiments, the proteins and other macromolecules associated with the biological membrane are in native state.

In some embodiments, the SUVs comprise lipid compositions including mixtures of any one or more components such as saturated and unsaturated phospholipids, phosphatidylethanolamines (PEs) and phosphatidylserines (PSs), phosphatidylcholine (PC), phosphoinositides, phosphatidylglycerols (PGs), sphingomyelins (SMs), sphingosine, ceramides, cerebrisides, gangliosides, and cholesterol.

In certain embodiments, the lipid bilayer has a fluidity, measured by FRAP, of at least 0.1 $\mu m^2/s$, such as at least 0.2 $\mu m^2/s$, at least 0.3 $\mu m^2/s$, at least 0.4 $\mu m^2/s$, at least 0.5 $\mu m^2/s$, at least 0.6 $\mu m^2/s$, at least 0.7 $\mu m^2/s$, at least 0.8 $\mu m^2/s$, at least 0.9 $\mu m^2/s$, at least 1 $\mu m^2/s$, at least 1.2 $\mu m^2/s$, at least 1.4 µm²/s, at least 1.6 µm²/s, at least 1.8 µm²/s, at least 2 µm²/s, at least 3 µm²/s, at least 4 µm²/s, or at least 5 µm²/s. In various embodiments, the lipid bilayer has a fluidity ranging between 0.1 µm²/s to 2 µm²/s, such as 0.1 µm²/s to 0.5 µm²/s, 0.1 µm²/s to 1 µm²/s, 0.1 µm²/s to 2 µm²/s, 0.3 µm²/s to 0.5 µm²/s, 0.3 µm²/s to 1 µm²/s, 0.3 µm²/s to 2 µm²/s, 0.5 µm²/s to 1 µm²/s, or 1 µm²/s to 2 µm²/s. In certain embodiments, the lipid bilayer has a fluidity ranging between about 0.3 µm²/s to about 1 µm²/s. In some embodiments, the fluidity of the bilayer as measured by FRAP is 0 µm²/s.

In some embodiments, the lipid bilayer is formed on a spacer molecule immobilized on the functionalization layer. In some embodiments, the size of the spacer molecule is selected such that the distance between the graphene layer and the upper surface of the lipid bilayer is larger than the sensing distance of the device. In some embodiments, the spacer molecule is a polymer, such as polyethyleneglycol (PEG). In some embodiments, the spacer molecule is a protein, such as BSA. In some embodiments, the spacer molecule is non-covalently adsorbed to the functionalization layer. In some embodiments, the spacer molecule is covalently immobilized to the functionalization layer. In some embodiments, the spacer molecule is covalently bound to the lipid bilayer. In some embodiments, the spacer molecule is non-covalently bound to the lipid bilayer.

Assembly of the Biosensor for Quantitative Measurement of IMP Function

In order to set up a biosensor for measurement of IMP function one of the following methods can be followed: a) a spacer molecule is positioned between the graphene layer and the lipid bilayer, and the size of the spacer molecule is selected to allow the upper surface of the lipid bilayer to be beyond the sensing distance of the device; b) a lipid bilayer is formed on the functionalization layer and the ionic strength of the aqueous medium is adjusted to cause the sensing distance to be less than the distance between the graphene layer and the upper surface of the lipid bilayer; c) a spacer molecule and an adjustment of the ionic strength of the aqueous medium are used in combination to allow the upper surface of the lipid bilayer to be beyond the sensing distance.

In various embodiments, the distance between the upper surface of the lipid bilayer and the graphene layer is larger than the sensing distance. In some of these embodiments, the distance between the lower surface of the lipid bilayer and the graphene layer is less than the sensing distance. In some of these embodiments the distance between the lower surface of the lipid bilayer and the graphene layer is larger than the sensing distance. In some of these embodiments the distance between the lower surface of the lipid bilayer and the graphene layer is equal to the sensing distance.

Tuning of the Biosensor for Quantitative Measurement of IMP Function

For the graphene biosensor described herein, the sensing distance of the device is related to the ionic strength of the aqueous medium, the Debye length, and the gating capacity of the system. Thus, the sensing distance of the device can be modulated by adjusting the ionic strength of the aqueous medium.

The device can be tuned by the use of a spacer molecule, an adjustment of the ionic strength of the medium, or a combination of an ionic strength adjustment and the use of a spacer molecule. In some embodiments, the device is tuned by an adjustment of the ionic strength of the aqueous medium alone. In some embodiments, the device is tuned by a combination of an adjustment of the ionic strength and the use of a spacer molecule. In some embodiments, the device is tuned by the use of a spacer molecule alone.

Methods of Use

Aspects of the subject disclosure include methods for using the biosensor to detect a drug or ligand binding effect on the function of a membrane protein. Examples of detectable events are shown in Table 1.

Characterizing an Agonist, an Antagonist, or an Inactive Ligand

In some embodiments, a ligand with unknown activity to an IMP can be characterized as an agonist, an antagonist, or an inactive ligand using the graphene biosensor as described herein.

In certain embodiments, the IMP is first exposed to a known agonist only, and then to both a known agonist and a known antagonist to define the baseline activities of the IMP. The ligand with unknown activity can then be tested. In some of these embodiments, when the ligand is tested alone and produces a detectable signal from the biosensor, the ligand can be characterized as an agonist. In some other of these embodiments, when the ligand does not produce a detectable signal when tested alone but competes for binding with a known agonist when tested together with the known agonist, the ligand can be characterized as an antagonist. In yet some other of these embodiments, when the ligand does not produce a detectable signal when tested alone and does not compete for binding with the known agonist when tested together with the known agonist, the ligand can be characterized as an inactive ligand.

Measuring a Conformational Change

Figure 3:
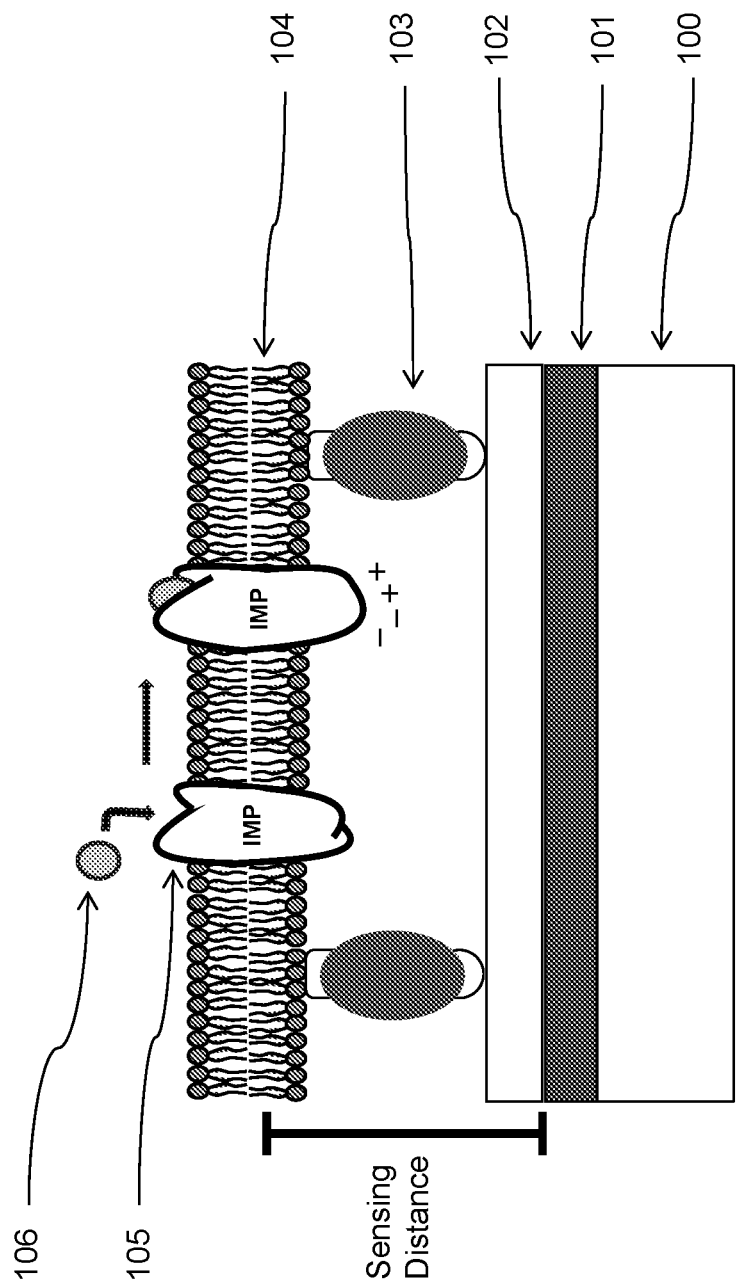
FIG. 3 provides an example where the binding of a ligand to an integral membrane protein (IMP) induces a conformational change which results in the exposure of charges on the surface of the IMP, with 100 representing the support substrate, 101 representing the graphene layer, 102 representing the functionalization layer, 103 representing the spacer molecule, 104 representing the lipid bilayer, 105 representing the IMP, and 106 representing the ligand. In the figure, the ligand binds to a site that is beyond the sensing distance and thus cannot be detected by the graphene sensor. In contrast, the newly exposed charges occur within the sensing space and can be detected by the graphene sensor.

In some embodiments, the binding of a ligand to an IMP induces a conformational change. In some of these embodiments, the conformational change leads to a net charge change or rearrangement of charges within the sensing space. In some of these embodiments, the conformational change results in exposure of the charges on the surface of the IMP within the sensing space. In certain embodiments, the net charge change or rearrangement of charges within the sensing space can be detected by the graphene biosensor (FIG. 3 and FIG. 4A).

Measuring a Protein-Protein Interaction

In some embodiments, the binding of a ligand to an IMP causes the formation or disruption of protein-protein interaction. In some of these embodiments, the formation or disruption of protein-protein interaction leads to a change in net charge or charge distribution within the sensing space. In certain embodiments, the net charge change or rearrangement of charges within the sensing space can be detected by the graphene biosensor (FIG. 4B).

Measuring an Enzymatic Activity

In some embodiments, the binding of a ligand to an IMP results in activation or inhibition of an enzymatic activity. In some of these embodiments, the activation or inhibition of an enzymatic activity results in a change in net charge or charge distribution in the sensing space. In certain embodiments, the activation or inhibition of an enzymatic activity leads to the generation of new ions within the sensing space. In certain embodiments, the activation or inhibition of an enzymatic activity leads to the rearrangement of charges within the sensing space. In certain embodiments, the net charge change or rearrangement of charges within the sensing space can be detected by the graphene biosensor (FIG. 4C).

Measuring a Transport Function

In some embodiments, ligand binding to an IMP results in activation or deactivation of an ion or solute channel or transporter, transporting ions or charged molecules across the lipid bilayer. In some of these embodiments, the activation or deactivation of the channel or transporter cause a change in net charge or charge distribution in the sensing space. In certain embodiments, the ions or charged molecules are transported into the sensing space, leading to an increase of charged species within the sensing space. In certain other embodiments, the ions or charged molecules are transported out of the sensing space, leading to a decrease of charged species within the sensing space. In certain embodiments, the net charge change or rearrangement of charges within the sensing space can be detected by the graphene biosensor (FIG. 4D).

Measuring Multiple Detectable Events

In some embodiments, one detectable event is induced by ligand binding to an IMP. In some other embodiments, two or more detectable events are induced by ligand binding to an IMP. In certain embodiments, the ligand binding can lead to one or more detectable events, including a conformational change, a formation or disruption of protein-protein interaction, an activation or inhibition of an enzymatic activity, and an activation or deactivation of an ion or solute channel or transporter. In some of these embodiments, each of the events can contribute to the signal by changing the net charge or charge distribution within the sensing space. In certain embodiments, the net charge change or rearrangement of charges within the sensing space can be detected by the graphene biosensor.

In certain specific embodiments, the ligand binding to an IMP induces a conformation change resulting in protein dissociation and enzymatic activity induced by the dissociated protein subunits. In some of these embodiments, the protein dissociation can also induce ion channel or transporter activity. In some of these embodiments, each of the events can contribute to the signal detected by the graphene biosensor by changing the net charge or charge distribution within the sensing space (FIG. 5).

In certain specific embodiments, the ligand binding to an IMP induces a conformational change resulting in dimerization through a protein-protein interaction with another ligand bound IMP. In some of these embodiments, the dimerization can induce a response such as enzymatic phosphorylation of the IMP domains on the other side of the lipid bilayer. In some of these embodiments, each of the events can contribute to the signal detected by the graphene biosensor by changing the net charge or charge distribution within the sensing space (FIG. 6).

EQUIVALENTS AND SCOPE

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of biophysics, surface chemistry, nanotechnology, protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pennsylvania: Mack Publishing Company, 1990); Carey and Sundberg Advanced Organic Chemistry 3rd Ed. (Plenum Press) Vols A and B (1992).

Example 1: Adjusting Ionic Strength to Fabricate a Biosensor for Quantitative Measurement of IMP Function In this example, PEG-PE of a defined molecular weight is used as a spacer molecule and, adjustment of buffer ionic strength is used to adjust the sensing distance of the biosensor such that the upper surface of the lipid bilayer is positioned outside of the sensing space. To prepare the biosensor the following steps are performed at room temperature.

Step 1—Membrane assembly:
a) Native membrane vesicles (NMVs) containing the IMP of interest, and small unilamellar vesicles (SUVs) containing 0.1-0.5% PEG-PE and 95-99.9% POPC, are prepared using methods well known in the art. In this example, PEG-PE with a molecular weight of 3,000 dalton is used as a spacer molecule incorporated into the SUV lipid bilayer to generate a cushion by its polyethylene glycol moiety.
b) The functionalization layer is cleaned by RIE.
c) NMVs in PBS buffer (137 mM NaCl; 2.7 mM KCl; 4.3 mM $Na_2HPO_4$; 1.47 mM $KH_2PO_4$; pH of 7.4) are exposed to the sensor surface and allowed to bind for up to 30 minutes. Unbound NMVs are washed away by gentle flow at 25 µl/min, with PBS buffer.
d) The surface is then incubated with SUVs in PBS buffer containing 5-20 mM EDTA for at least 20 minutes to allow formation of a lipid bilayer covering the sensor. Excess SUVs are washed away by flowing PBS buffer at 25 µl/min for 5 minutes. The PEG moieties attached to the lipid bilayer increase the distance between the graphene surface and the upper surface of the lipid bilayer.
e) The sensor is allowed to equilibrate by flowing a diluted PBS buffer with low ionic strength, such as 0.5% PBS, for 15 minutes or until a stable baseline signal is obtained. All steps are performed at room temperature.

Step 2—Adjusting sensing distance: After assembling the lipid bilayer, the ionic strength of the buffer is adjusted higher until binding of a test ligand, such as an antibody, to an epitope on the upper surface of the lipid bilayer is not detected. It is important to select an antibody that is known not to induce any signal transduction response upon binding for this test. An epitope tag such as Flag-tag or His-tag attached to the target IMP is particularly useful for this test as antibody binding to epitope tags on an IMP often result in no signal transduction. To adjust the sensing distance:
a) Flow 0.5% PBS buffer, at 25 µl/min until a stable baseline is achieved
b) Flow the anti-tag antibody at a fixed concentration, e.g. 100 nM in 0.5% PBS buffer for 5 minutes or until the signal reaches a plateau.
c) Record the plateau binding signal at this buffer concentration. If no anti-tag antibody binding signal is detected with 0.5% PBS, a lower concentration of PBS can be tried such as 0.2% PBS, or the lipid bilayer is prepared with smaller spacer molecule such as 1,000 dalton PEG-PE to lower the upper surface of the lipid bilayer until binding of the anti-tag antibody is detected.
d) Flow 0.5% PBS buffer to allow anti-tag antibody dissociation until signal returns to baseline.
e) Repeat the anti-tag antibody binding test ("a" through "d") with increasing buffer concentrations (e.g. 1%, 2%, 4%, 10%, 25% PBS) until no binding signal is detected. In each cycle, the sensor is equilibrated with the desired buffer strength and exposed to 100 nM anti-tag antibody in the same desired buffer strength, the binding signal is recorded, and the antibody is dissociated until signal returns to baseline as before.

Step 3—Verify detection of signal transduction induced by a known agonist ligand. This test is conducted at a buffer ionic strength where the upper surface of the lipid bilayer is outside of the sensing space, and the lower surface of the lipid bilayer is 4-10 nm closer to the graphene surface and within the sensing space. Thus, only response signal generated within the sensing space is measured.
a) To measure ligand-induced signal generated below the lipid bilayer without detecting ligand binding to the upper surface of the lipid bilayer, use results from Step 2 to select a buffer ionic strength that is just high enough to avoid detection of anti-tag antibody binding. Then flow the selected buffer strength to equilibrate the sensor for 5 minutes or until a stable baseline is reached.
b) Verify the performance of the sensor by testing the binding of a ligand known to induce signal transduction upon binding to the target IMP, such as a known agonistic anti-IMP therapeutic antibody or small molecule. The agonistic ligand is tested in the selected buffer strength at concentrations equal to 0.3, 1, 3, and 10 times the expected $K_D$ value for the interaction between the agonistic ligand and the IMP. The resulting sensor response corresponds to ligand induced signal transduction measured within the sensing space.
c) After verifying the response with the known agonistic ligand the sensor is ready to test unknown ligands under the same selected buffer strength.

Example 2: Adjusting Spacer Molecule Size to Fabricate a Biosensor for Quantitative Measurement of IMP Function In this example a combination of adjusting spacer molecule size and adjusting buffer ionic strength, is used to prepare a sensor where the upper surface of the lipid bilayer is positioned outside of the sensing space, and the lower surface of the lipid bilayer is closer to the graphene layer and within the sensing space. To prepare the biosensor the following steps are performed:

Step 1—Membrane assembly:
a) In this example separate sensor chips are used to assemble lipid bilayers using 4 different sizes of PEG-PE as spacer molecules. For example, PEG-PE with molecular weights of 1,000 dalton, 2,000 dalton, 3,000 dalton, and 5,000 dalton are used to obtain different distances between the graphene layer and the upper surface of the lipid bilayer. Native membrane vesicles (NMVs) containing the IMP of interest are prepared as above. A separate small unilamellar vesicle (SUV) preparation is generated as described in example 1 for each of the PEG-PE molecular weights to be tested. SUV preparations are labeled "SUV1000", "SUV2000", "SUV3000", and "SUV5000" respectively.
b) The functionalization layer is cleaned by RIE.
c) For all 4 chips, NMVs in PBS buffer (137 mM NaCl; 2.7 mM KCl; 4.3 mM $Na_2HPO_4$; 1.47 mM $KH_2PO_4$;

pH of 7.4) are exposed to the sensor surface and allowed to bind for up to 30 minutes. Unbound NMVs are washed away by gentle flow at 25 µl/min, with PBS buffer.

d) The surface of the 4 chips are then incubated, each with one of the 4 SUV preparations in PBS buffer containing 5-20 mM EDTA for at least 20 minutes to allow formation of a lipid bilayer covering the sensor. Excess SUVs are washed away by flowing PBS buffer at 25 µl/min for 5 minutes. Membranes assembled using higher PEG-PE molecular weight will have a larger distance between the graphene layer and the upper surface of the lipid bilayer.

e) The sensors are allowed to equilibrate by flowing a diluted PBS buffer with low ionic strength, such as 3% PBS, for 15 minutes or until a stable baseline signal is obtained. All steps are performed at room temperature.

Step 2—Selecting spacer size and Adjusting sensing distance:

a) After assembling the 4 lipid bilayers containing different PEG-PE spacers, binding of the anti-tag antibody is tested as in Example 1 on all 4 chips at the same buffer strength, e.g. 3% PBS. If all membranes show a response, the test is repeated at a higher ionic strength such as 5% PBS. If none of the membranes show a response, then the test is repeated at a lower ionic strength such as 1% PBS. Different ionic strengths are tried until a mixed set of responses is obtained at a given ionic strength. Then the signal obtained with each of the membranes is compared, and membranes that do not show a response are identified. From the membranes that do not show a response, the one prepared with the highest molecular weight PEG-PE as a spacer is selected.

b) If desired, after selecting a membrane with a specific PEG-PE spacer size, additional fine tuning of the sensing distance can be performed for the selected membrane by making small adjustments (e.g. plus or minus 0.2% PBS) to the buffer ionic strength and testing anti-tag antibody binding following the procedure described in Example 1, Step 2 to select the highest ionic strength that will not result in an anti-tag antibody binding signal.

Step 3—Verify detection of signal transduction induced by a known ligand. This test is conducted with spacer molecular weight and ionic strength selected above where the upper surface of the lipid bilayer is outside of the sensing space, and the lower surface of the lipid bilayer is 4-10 nm closer to the graphene surface and within the sensing space. Thus, only response signals generated within the sensing space can be measured.

a) To measure ligand-induced signal generated below the lipid bilayer without detecting ligand binding to the upper surface of the lipid bilayer, flow the selected buffer strength to equilibrate the sensor for 5 minutes or until a stable baseline is reached.

b) Verify the performance of the sensor by testing the binding of a ligand known to induce signal transduction upon binding to the target IMP, such as a known agonistic anti-IMP therapeutic antibody or small molecule. The agonistic ligand is tested in the selected buffer strength at concentrations equal to 0.3, 1, 3, and 10 times the expected $K_D$ value for the interaction between the agonistic ligand and the IMP. The resulting sensor response corresponds to ligand induced signal transduction measured within the sensing space.

c) After verifying the response with the known agonistic ligand the sensor is ready to test unknown ligands under the same selected buffer strength.

Example 3: Quantitative Measurement of IMP Function with the Biosensor

Characterizing EGFR Ligands as Agonists, Antagonists, or Inactive Ligands

Tyrosine kinase receptors (TKR) are an important family of IMPs which are often the target for therapeutic discovery efforts in oncology and other therapeutic areas. Several commercial anti-cancer antibody drugs such as Herceptin® and cetuximab target TKRs. During the development of new drugs targeting IMPs, it is essential to distinguish agonists from antagonists and inactive ligands. This example illustrates how the methods described herein are used to characterize the effect of various ligands on the function of an IMP such as EGFR. To determine if EGFR ligands are agonists, antagonists, or inactive ligands, the following procedure is provided.

Step 1—Assemble EGFR expressing membranes and adjust sensing distance a) EGFR Membrane Assembly. NMVs are prepared from a cell line expressing EGFR, such as A431 epidermoid carcinoma cells, by methods well known in the arts. A431-MNVs are used with SUVs to form a lipid bilayer covering the device's sensor as described in Example 1.

b) Adjusting Sensing Distance. Mouse monoclonal antibody clone M225 binds to the extracellular domain of EGFR, however it does not induce signal transduction. Instead, M225 acts as an antagonist blocking binding of EGF, preventing receptor dimerization and kinase activation. After following the procedure described in Example 1 to form a lipid bilayer using A431-NMVs, M225 is used as a test antibody to adjust the ionic strength of PBS buffer as described in example 1. PBS buffer strength is adjusted to a level just high enough so that the binding of M225 to the upper surface of the lipid bilayer is not detected. This PBS concentration is selected to perform testing of EGFR ligands.

c) The performance of the sensor at the selected PBS strength is measured by testing the signal resulting from binding of EGF to EGFR. EGF is the natural agonist of EGFR and will induce a signal transduction response. As illustrated in FIG. 6, binding of EGF to the extracellular domain of EGFR results in signal transduction by inducing conformational changes, receptor dimerization (protein-protein interaction), activation of its intracellular kinase domains, and autophosphorylation of its c-terminal domain. For simplicity, ATP is omitted from the buffer to prevent autophosphorylation. Thus any detectable signal in this assay is the result of ligand-induced conformational changes and dimerization protein-protein interactions. The EGF- EGFR interaction has an approximate $K_D$ of 1 nM. EGF signal transduction response is measured at 0.1 nM, 0.3 nM, 1 nM, 3 nM, 10 nM, 30 nM and 100 nM EGF to generate a response curve and the maximum level of response is determined.

Step 2—Characterization of the activity of test ligands as agonists, antagonists, or inactive ligands.
 a) The maximum signal level observed with EGF is defined as 100% activity; and signal, if any, produced by M225 at 250 nM, is defined as baseline or 0% activity. To further verify the performance of the sensor the following experiment is performed: 250 nM antibody M225 is allowed to bind to EGFR first for 5 minutes at 25 µl/min, immediately followed by 10 nM EGF for 5 min at 25 µl/min, and the signal level is recorded. Binding of M225 will result in no signal, however, because M225 is an antagonist that prevents binding of EGF, a smaller than 100% activity, will be detected when EGF binds after M225 when compared to binding of 10 nM EGF alone. A percentage of inhibition by the M225 antagonist is then calculated.
 b) A series of ligands with unknown activity are now tested and characterized at various concentrations to determine maximum signal, if any. For example ligands are tested alone at 0.1 nM, 0.3 nM, 1 nM, 3 nM, 10 nM, 30 nM and 100 nM, and maximum signal (if any) is recorded. Ligands inducing a detectable signal are classified as agonists, and their maximum response is compared to the maximum response of EGF and further classified as strong agonists or weak agonists accordingly. Ligands that do not induce a signal are now tested to discern inactive ligands from antagonists. Ligands are first allowed to bind to EGFR at a high concentration such as 250 nM for 5 minutes at 25 µl/min, immediately followed by 10 nM EGF for 5 min at 25 µl/min. Ligands that cause an EGF induced signal of less than 100% have antagonist activity, and can be further classified as strong antagonists or weak antagonists accordingly. Ligands that do not affect EGF induced signal are considered inactive.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

TABLE 1

Examples of Detectable Events

| IMP Type | Examples | Activity/Response | "Ionic Status" Change Induced By: |
|---|---|---|---|
| GPCR | B2AR | Conformational change | Charge rearrangements |
|  |  | Protein-protein interactions | Charge rearrangements |
|  |  | Adenyl cyclase ATP hydrolysis, | Ion generation (PPI) |
|  |  | GTP hydrolysis | Ion generation (PPI) |
| Ion Channels | Na, K, H, Ca channels | Conformational change | Charge rearrangements |
|  |  | Ion flow | Influx/outflow of ions |
| Transporters | MDR-1, MRP | Conformational change | Charge rearrangements |
|  |  | Drugs, xenobiotics eflux | Outflow of metabolites |
|  |  | ATP hydrolysis | Ion generation (PPI) |
| Tyrosine kinase receptors | EGFR, FGFR, ErbB, VEGFR | Conformational change | Charge rearrangements |
|  |  | Dimerization | Ion generation |
|  |  | Protein-protein interactions |  |
|  |  | Kinase, phosphorylation, ATP hydrolysis |  |

The invention claimed is:

1. A device, comprising:
 a support substrate;
 a graphene layer, said graphene layer deposited on said support substrate;
 a functionalization layer, said functionalization layer deposited on at least a portion of said graphene layer;
 a lipid bilayer comprising:
  an upper leaflet surface, a lower leaflet surface and a hydrophobic interior volume bounded by said upper leaflet and said lower leaflet surfaces;
 a membrane protein associated with said lipid bilayer;
 a spacer molecule interposed between said lipid bilayer and said functionalization layer; and
 electrodes in electrical contact with said graphene layer, said electrodes adapted to detect an electrical signal from said graphene layer,
 wherein said spacer molecule establishes a distance between said lipid bilayer and graphene layer, wherein said distance permits detection of an electrical signal associated with a functional or structural change in said membrane protein upon binding of a test agent to said membrane protein.

2. The device of claim 1, wherein said functionalization layer comprises solid state material.

3. The device of claim 1 or 2, wherein said membrane protein is an integral membrane protein.

4. The device of claim 1 or 2, wherein said membrane protein is a peripheral membrane protein.

* * * * *